US00PP26536P3

(12) United States Plant Patent
Olesen

(10) Patent No.: US PP26,536 P3
(45) Date of Patent: Mar. 29, 2016

(54) COMPACT FLORIBUNDA ROSE PLANT NAMED 'POULPAL056'

(50) Latin Name: ***Rosa* hybrid**
Varietal Denomination: Poulpal056

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 248 days.

(21) Appl. No.: 13/986,922

(22) Filed: Jun. 14, 2013

(65) Prior Publication Data

US 2014/0373225 P1 Dec. 18, 2014

(51) Int. Cl.
*A01H 5/00* (2006.01)
*A01H 5/02* (2006.01)

(52) U.S. Cl.
USPC ..... Plt./145
CPC ..... *A01H 5/0222* (2013.01)

(58) Field of Classification Search
USPC ..... Plt./145
See application file for complete search history.

(56) References Cited

PUBLICATIONS

Palace Perfection by Poulsen. 2012-2013.*

* cited by examiner

*Primary Examiner* — Annette Para

(57) ABSTRACT

A new garden rose plant of the Compact Floribunda class which has abundant, yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal056'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2004 and the resulting seeds were planted in a controlled environment in Fredensborg, Denmark. The new variety, named 'Poulpal056', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots; and
3. Exceptional disease resistance.

This combination of qualities is not present in previously available commercial cultivars of this type, known to the inventor, and distinguish 'Poulpal056' from all other varieties of which we are aware.

As part of the rose development program, Mogens N. Olesen germinated the seeds from the aforementioned hybridization during winter of 2004 and conducted evaluations on the resulting seedlings in a controlled environment in Fredensborg, Denmark. 'Poulpal056' was selected in the spring of 2005 by the inventor as a single plant from the progeny of the aforementioned hybridization.

Asexual reproduction of 'Poulpal056' by traditional budding and rooted cuttings was first done by Mogens N. Olesen in the nursery in Fredensborg, Denmark in July, 2005. This initial and other subsequent asexual propagations conducted in controlled environments have demonstrated that the characteristics of 'Poulpal056' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal056'.

Specifically illustrated in FIG. 1 are flower in parts.

DETAILED DESCRIPTION OF THE VARIETY

Figure 1:
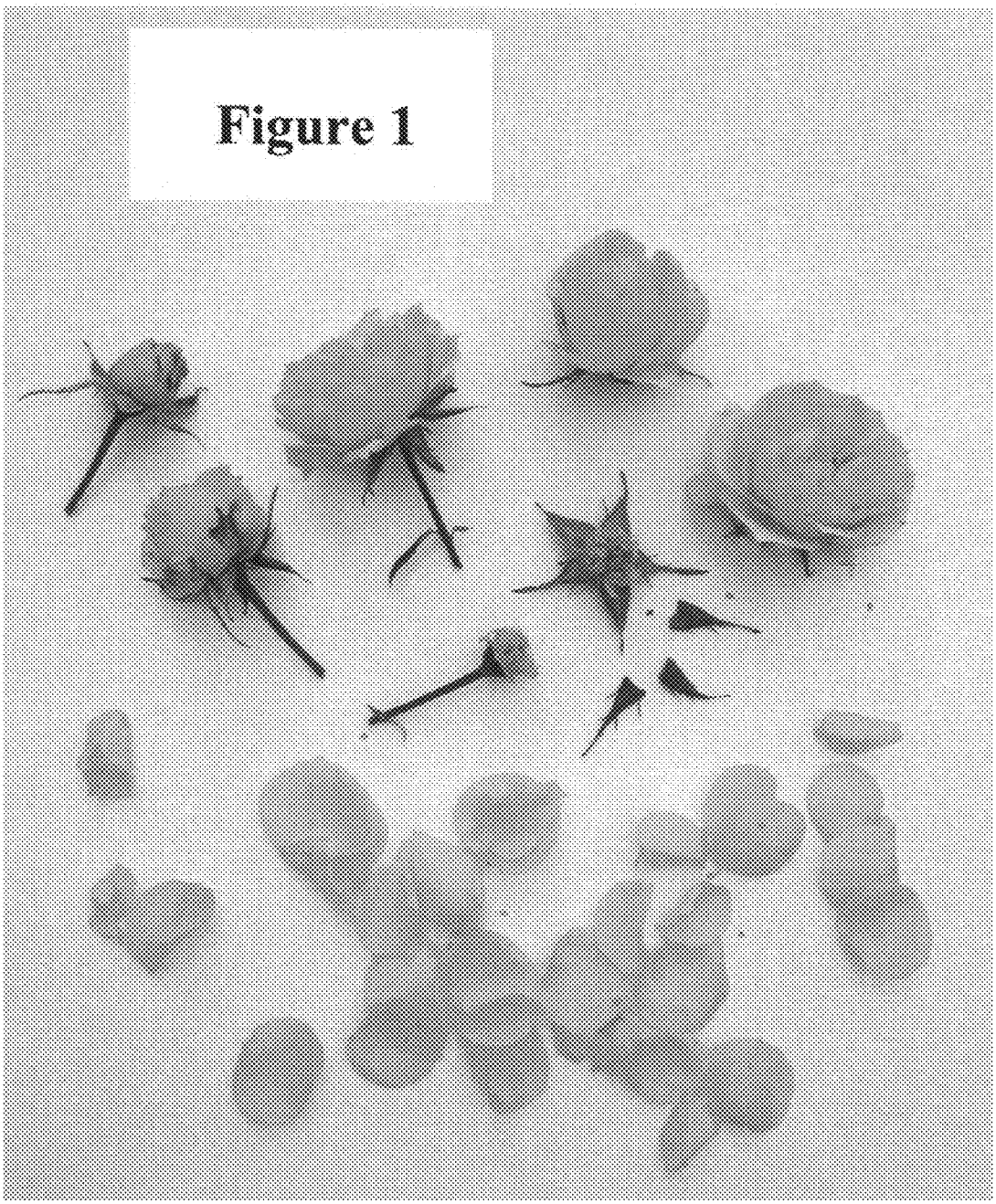
Figure 2:
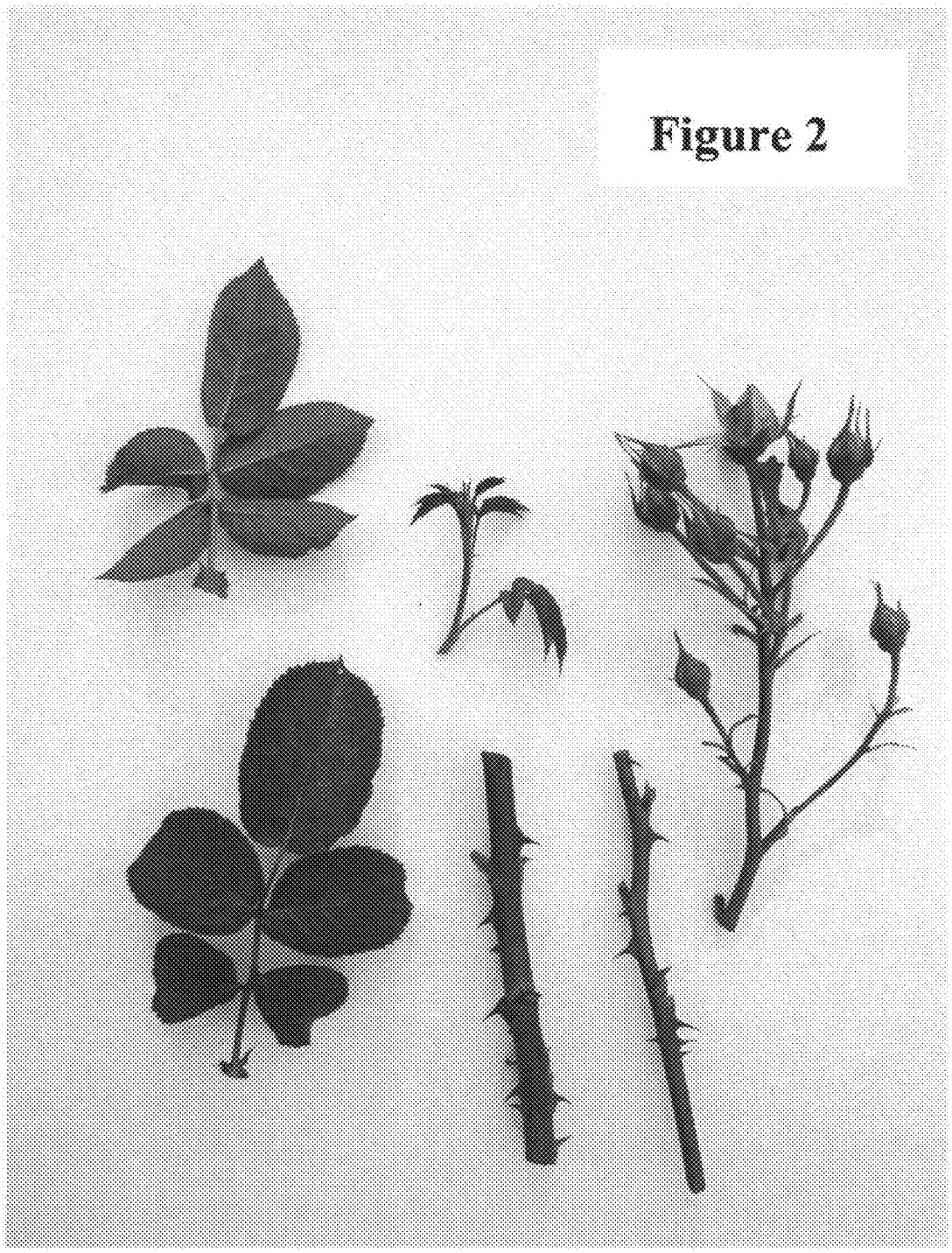
FIG. 2 is leaves and stems.

The following is a description of 'Poulpal056', as observed in its growth in in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulsiana', U.S. Plant Pat. No. 11,638 are compared to 'Poulpal056' in Chart 1.

CHART 1

| | 'Poulpal056' | 'Poulsiana' |
|---|---|---|
| Petal Count | 50 petals | 15 to 20 petals |
| Flower Diameter | 50 to 60 mm | 55 to 60 mm |
| General Tonality of Flower Color | Yellow Group 12A | Yellow Group 7C |

FLOWER AND FLOWER BUD

Blooming habit: Continuous.

Flower bud:

*Size*.—Upon opening, 18 mm in length from base of receptacle to end of bud. Bud diameter is 15 mm.

*Bud form*.—Globose.

*Bud color*.—As sepals divide petals are Yellow-Orange Group 14C with intonations of Orange 29A and Orange-Red Group N34A.

*Sepal inner surface*.—Color: Green Group 138B. Surface: Smooth. Moderate pubescence.

*Sepal outer surface*.—Color: Yellow-Green Group 144A with moderate intonations of Greyed-Red Group 179A. Texture: Smooth.

*Sepal shape*.—Apex: Cirrhose. Base: Flat at union with receptacle.

*Sepal margin*.—Margins have weak to moderate moderate foliaceous appendages on three of the five sepals.

*Sepal size*.—25 mm long by 9 mm wide.

*Receptacle*.—Texture: Smooth. Size: 4 mm in height by 9 mm wide. Color: Yellow-Green Group 144A. Anthocyanic pigments the color of Greyed-Red Group 179A. Shape: Broadly campanulate.

*Pedicel*.—Surface: Smooth. Length: About 50 mm. Diameter: 3 mm on average. Color: Yellow-Green Group 144A. Strength: Strong.

*Peduncle*.—Length: 4 to 15 cm. Diameter: 4 to 5 mm. Color: Yellow-Green Group 144A.

Flower bud development: Flower buds are borne in clusters of 11 to 25 flower buds per stem, resembling a panicle.

Flower bloom:

*Fragrance*.—Medium honey and floral scent.

*Duration*.—The blooms have a duration on the plant of approximately 14 days. Petals fall cleanly away from plant after flowers have fully matured.

*Size*.—Flower diameter is 50 to 60 mm when open. Flower depth is 25 mm.

*Flower shape*.—General shape is a quartered rosette with many overlapping petals packed into quarter sections.

*Shape of flower, side view*.—Upper portion is flat. The lower portion is concave.

Petalage: Under normal conditions, flowers have 50 petals total, 10 of which are petaloids.

General tonality of flower: Open flowers are Yellow Group 12A. Tonality changes to Yellow Group 8B as the flower ages.

Petal color:

*Upon opening, outer petals*.—Upper surface: Yellow Group 9A at basal and middle zone. Yellow Group 8A at marginal zone. Lower surface: Yellow Group 13C.

*Upon opening, inner petals*.—Upper surface: Yellow Group 12A. Lower surface: Yellow Group 13B. No distinctive coloration at the petal base observed.

*After opening, inner and outer petals*.—Upper surface: Yellow Group 8A and 8C. Lower surface: Yellow Group 8C. No distinctive coloration at the petal base observed.

Petals:

*Petal reflex*.—Slight to none.

*Margin*.—Entire. Strong undulations of margin observed.

*Shape*.—Broadly acute. Apex shape: Rounded. Base shape: Acute.

*Size*.—26 mm (l) 30 mm (w).

*Texture*.—Smooth.

*Thickness*.—Average.

Petaloids:

*Size*.—20 mm (l) by 15 mm (w).

*Quantity*.—About 10.

*Shape*.—Asymmetric. Apex is rounded, base is acute.

*Color*.—Upper surface is Yellow Group 8A and 8C. Lower surface is Yellow Group 8C.

Reproductive organs:

*Pollen*.—None observed.

*Anthers*.—Size: 3 mm in length. Color: Yellow Group 11B. Quantity: 60 on average.

*Filaments*.—Color: Yellow-Orange Group 15A. Length: 7 mm.

*Pistils*.—Length: 5 mm. Quantity: 45 on average.

*Stigmas*.—Color: Greyed-Yellow Group 162B.

*Styles*.—Color: Yellow-Green Group 145D.

*Location of stigmas*.—Inferior in location relative to the length of the filaments and the height of the anthers.

*Hips*.—None Observed.

PLANT

Plant growth: Upright, bushy. Plants are 50 cm in height, and 50 cm wide.

Stems:

*Color*.—Juvenile growth: Yellow-Green Group 144A. Mature growth: Yellow-Green Group 146A with moderate to strong anthocyanin the color of Greyed-Orange Group 176B.

*Length*.—On average, canes are 40 cm from the base of the plant to the flowering portion.

*Diameter*.—8 mm.

*Internodes*.—On mature canes, there is an average distance of 40 mm between nodes.

*Surface texture*.—Young wood: Smooth. Older wood: Smooth.

Long prickles:

*Incidence*.—9 prickles per 10 cm of stem.

*Size*.—Average length of prickles on mature stems is 9 mm.

*Shape*.—Upper portion is linear. Lower portion is concave.

*Color*.—Juvenile prickles: Greyed-Red Group 180B. Mature prickles: Greyed-Red Group 179B.

Plant foliage:

*Compound leaf*.—185 mm (l)×145 (w) average.

*Quantity*.—2 leaves per 10 cm of stem on average.

*Leaf bearing angle to the stem*.—90 degrees.

*Color of juvenile foliage*.—Upper and Lower side: Yellow-Green Group 144B with Greyed-Red Group 178A generalized.

*Color of mature foliage*.—Upper side: Yellow-Green Group 146A. Lower side: Yellow-Green Group 146C.

Plant leaves and leaflets:

*Stipules*.—Size: 25 mm in length. Quantity: 2 per compound leaf. Shape: Linear, slightly broad based with outward extending apecies. Margins: Finely serrated with many stipitate glands. Color: Green Group 143B, with Greyed-Purple Group 183A.

*Petiole*.—Length: 50 mm. Diameter: 3 mm.

*Upper surface*.—Color: Yellow-Green Group 144B.

*Lower surface*.—Color: Yellow-Green Group 144C. Observations: Few prickles observed.

*Rachis*.—Length: 50 mm. Upper surface: Yellow-Green Group 144B. Lower surface: Yellow-Green Group 144C with few prickles.

*Leaflet*.—Quantity: Normal number of leaflets leaves in middle of the stem is 5 leaflets. Margins: Serrated. Size: Average size of the terminal leaflet on normal leaves is 75 mm in length by 60 mm wide. Shape: Generally ovate to elliptical. Base: Rounded, occasionally cordate. Apex: Mucronate. Texture: Smooth. Thickness: Average. Arrangement: Odd pinnate. Venation: Reticulate. Glossiness: Very Glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Compact Floribunda rose class named 'Poulpal056', substantially as illustrated and described herein, due to its abundant yellow flowers, disease resistance, and extended period of bloom.

* * * * *